(12) United States Patent
Stubbs et al.

(10) Patent No.: US 8,170,670 B2
(45) Date of Patent: *May 1, 2012

(54) SYSTEM AND METHOD FOR RECOVERING FROM TRANSIENT FAULTS IN AN IMPLANTABLE MEDICAL DEVICE

(75) Inventors: Scott R. Stubbs, Maple Grove, MN (US); Conrad L. Sowder, Minneapolis, MN (US); William J. Linder, Golden Valley, MN (US); Lynn S. Elliott, Maple Grove, MN (US); Kenneth P. Hoyme, Plymouth, MN (US); Hiten J. Doshi, Plymouth, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 655 days.

This patent is subject to a terminal disclaimer.

(21) Appl. No.: 12/359,757

(22) Filed: Jan. 26, 2009

(65) Prior Publication Data

US 2009/0132061 A1 May 21, 2009

Related U.S. Application Data

(63) Continuation of application No. 11/123,246, filed on May 5, 2005, now Pat. No. 7,483,744.

(51) Int. Cl.
*A61N 1/37* (2006.01)
(52) U.S. Cl. .................................. 607/27; 607/2; 607/59
(58) Field of Classification Search .................. None
See application file for complete search history.

(56) References Cited

U.S. PATENT DOCUMENTS

| | | | |
|---|---|---|---|
| 4,164,946 | A | 8/1979 | Langer |
| 5,074,301 | A | 12/1991 | Gill |
| 5,571,141 | A | 11/1996 | McNeil et al. |
| 5,653,735 | A | 8/1997 | Chen et al. |
| 5,735,882 | A | 4/1998 | Rottenberg et al. |
| 6,128,528 | A | 10/2000 | Erickson et al. |
| 6,128,530 | A | 10/2000 | Galen et al. |
| 6,198,968 | B1 | 3/2001 | Prutchi et al. |
| 6,456,875 | B1 | 9/2002 | Wilkinson et al. |
| 6,532,389 | B1 | 3/2003 | Shahandeh |

(Continued)

FOREIGN PATENT DOCUMENTS

EP  0753327 A2  1/1997

(Continued)

OTHER PUBLICATIONS

"U.S. Appl. No. 10/806,719, Supplemental Notice of Allowability mailed Nov. 9, 2007", 3 pgs.

(Continued)

*Primary Examiner* — Kennedy Schaetzle
(74) *Attorney, Agent, or Firm* — Schwegman, Lundberg & Woessner, P.A.

(57) ABSTRACT

A system and method is disclosed for system fault recovery by an implantable medical device which employs a global fault response. The system enables the device to consistently recover from transient faults while maintaining a history of the reason for the device fault. Upon detection of a fault, the primary controller of the device signals a reset controller which then issues a reset command. All sub-systems of the primary device controller are then reset together rather than resetting individual sub-systems independently to ensure deterministic behavior.

18 Claims, 4 Drawing Sheets

U.S. PATENT DOCUMENTS

| | | | |
|---|---|---|---|
| 6,584,355 | B2 | 6/2003 | Stessman |
| 6,635,048 | B1 | 10/2003 | Ullestad et al. |
| 7,363,080 | B2 | 4/2008 | Stubbs et al. |
| 7,373,200 | B2 | 5/2008 | Stubbs et al. |
| 7,383,087 | B2 | 6/2008 | Hoyme et al. |
| 7,483,744 | B2 * | 1/2009 | Stubbs et al. .................. 607/27 |
| 2002/0032470 | A1 | 3/2002 | Linberg |
| 2003/0036776 | A1 | 2/2003 | Foster et al. |
| 2003/0135244 | A1 | 7/2003 | Esler |
| 2003/0176894 | A1 | 9/2003 | Stahmann et al. |
| 2004/0138724 | A1 | 7/2004 | Sieracki et al. |
| 2005/0216063 | A1 | 9/2005 | Hoyme et al. |
| 2006/0253009 | A1 | 11/2006 | Stubbs et al. |
| 2006/0253158 | A1 | 11/2006 | Stubbs et al. |
| 2006/0253163 | A1 | 11/2006 | Stubbs et al. |
| 2008/0103542 | A1 | 5/2008 | Hoyme et al. |

FOREIGN PATENT DOCUMENTS

WO      WO-2006/121898 A1      11/2006

OTHER PUBLICATIONS

"U.S. Appl. No. 10/806,719, Advisory Action mailed May 12, 2006", 3 pgs.

"U.S. Appl. No. 10/806,719, Advisory Action mailed May 23, 2007", 3 pgs.

"U.S. Appl. No. 10/806,719, Final Office Action mailed Feb. 7, 2007", 10 pgs.

"U.S. Appl. No. 10/806,719, Final Office Action mailed Mar. 7, 2006", 9 pgs.

"U.S. Appl. No. 10/806,719, Non-Final Office Action mailed Jul. 17, 2006", 10 pgs.

"U.S. Appl. No. 10/806,719, Non-Final Office Action mailed Nov. 3, 2005", 9 pgs.

"U.S. Appl. No. 10/806,719, Notice of Allowance mailed Sep. 14, 2007", 4 pgs.

"U.S. Appl. No. 10/806,719, Response filed Feb. 1, 2006 to Non-Final Office Action mailed Nov. 3, 2005", 15 pgs.

"U.S. Appl. No. 10/806,719, Response filed May 8, 2006 to Final Office Action mailed Mar. 7, 2006", 12 pgs.

"U.S. Appl. No. 10/806,719, Response filed May 16, 2007 to Final Office Action mailed Feb. 7, 2007", 16 pgs.

"U.S. Appl. No. 10/806,719, Response filed Oct. 13, 2006 to Non-Final Office Action mailed Jul. 17, 2006", 12 pgs.

"U.S. Appl. No. 11/122,970, Notice of Allowance Malied Dec. 19, 2007", 4 pgs.

"U.S. Appl. No. 11/122,970, Response filed Sep. 28, 2007 to Non-Final Office Action mailed Jun. 28, 2007", 7 pgs.

"U.S. Appl. No. 11/122,970, Non-Final Office Action mailed Jun. 28, 2007", 10 pgs.

"U.S. Appl. No. 11/122,982, Notice of Allowance Mailed Nov. 27, 2007", 4 pgs.

"U.S. Appl. No. 11/122,982, Response filed Sep. 28, 2007 to Non-Final Office Action mailed Jun. 28, 2007", 8 pgs.

"U.S. Appl. No. 11/122,982, Non Final Office Action mailed Jun. 28, 2007", 10 pgs.

"U.S. Appl. No. 11/123,246. Response filed May 27, 2008 to Non-Final Office Action mailed Feb. 25, 2008", 8 pgs.

"U.S. Appl. No. 11/123,246, Non-Final Office Action mailed Feb. 25, 2008", 7 pgs.

"U.S. Appl. No. 11/123,246, Notice of Allowance mailed Sep. 17, 2008", 4 pgs.

"European Application Serial No. 06759185.9, Communication mailed Mar. 31, 2008", 3 pgs.

"European Application Serial No. 06759185.9, Response filed Oct. 10, 2008 to Communication mailed Mar. 31, 2008", 7 pgs.

"International Search Report and Written Opinion for Application No. PCT/US2006/017486, Date Mailed Aug. 30, 2006", 11 pgs.

* cited by examiner

SYSTEM AND METHOD FOR RECOVERING FROM TRANSIENT FAULTS IN AN IMPLANTABLE MEDICAL DEVICE

CROSS REFERENCE TO RELATED APPLICATIONS

This application is a continuation of U.S. application Ser. No. 11/123,246, filed May 5, 2005, now issued as U.S. Pat. No. 7,483,744, which is hereby incorporated by reference in its entirety.

This application is related to the following applications, both filed on May 5, 2005 and both hereby incorporated by reference in their entirety: "SYSTEM AND METHOD FOR PROVIDING TACHYARRHYTHMIA THERAPY BY IMPLANTABLE DEVICE IN PRESENCE OF SYSTEM FAULTS", Ser. No. 11/122,970, now issued as U.S. Pat. No. 7,373,200, and "SYSTEM AND METHOD FOR PROVIDING BRADYCARDIA THERAPY BY IMPLANTABLE DEVICE IN PRESENCE OF SYSTEM FAULTS", Ser. No. 11/122,982, now issued as U.S. Pat. No. 7,363,080.

FIELD OF THE INVENTION

This invention pertains to systems and methods for operating implantable medical devices.

BACKGROUND

Cardiac rhythm management devices (CRMDs) are implantable devices that provide electrical stimulation to selected chambers of the heart in order to treat disorders of cardiac rhythm. A pacemaker, for example, is a cardiac rhythm management device that paces the heart with timed pacing pulses. The most common condition for which pacemakers are used is in the treatment of bradycardia, where the ventricular rate is too slow. Atrio-ventricular conduction defects (i.e., AV block) that are permanent or intermittent and sick sinus syndrome represent the most common causes of bradycardia for which permanent pacing may be indicated. If functioning properly, the pacemaker makes up for the heart's inability to pace itself at an appropriate rhythm in order to meet metabolic demand by enforcing a minimum heart rate and/or artificially restoring AV conduction. Pacing therapy may also be delivered for the purpose of restoring synchronous ventricular contractions in patients with inter-ventricular or intra-ventricular conduction disorders, termed cardiac resynchronization therapy. Other cardiac rhythm management devices are designed to detect atrial and/or ventricular tachyarrhythmias and deliver electrical stimulation in order to terminate the tachyarrhythmia in the form of a cardioversion/defibrillation shock or anti-tachycardia pacing. Certain combination devices may incorporate any or all of the above functionalities.

CRMD's are complex electronic devices which are subject to failures of various kinds after implantation. It is desirable for such devices to be able to detect when these failures occur and then take action which minimizes harm to the patient.

SUMMARY

A system and method is disclosed for system fault recovery by an implantable medical device which employs a global fault response. The system enables the device to consistently recover from transient faults while maintaining a history of the reason for the device fault. Upon detection of a fault, the primary controller of the device signals a reset controller which then issues a reset command. All sub-systems of the primary device controller are then reset together rather than resetting individual sub-systems independently to ensure deterministic behavior.

DETAILED DESCRIPTION

Figure 1:
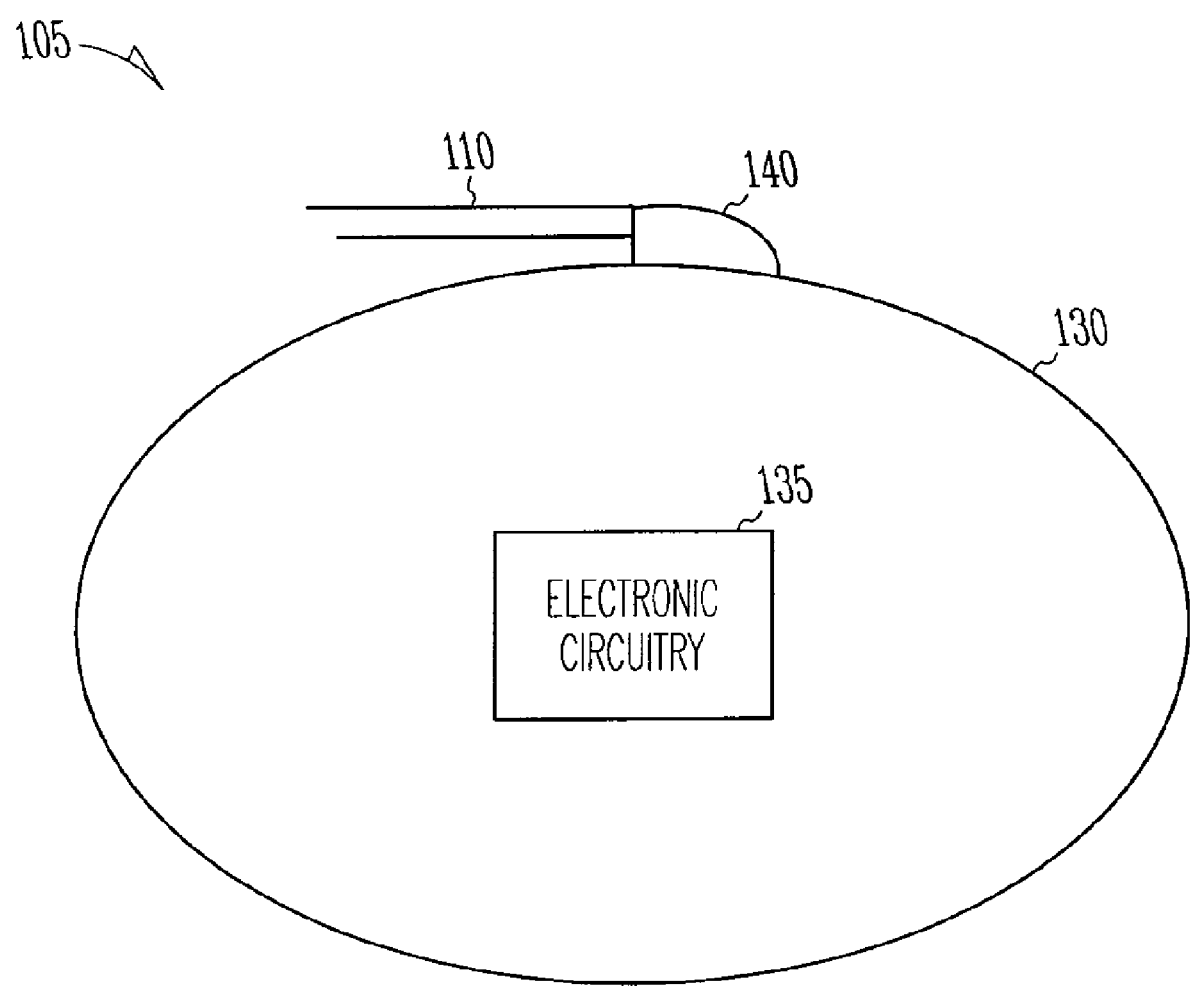
FIG. 1 illustrates the physical configuration of an exemplary implantable device.

Implantable cardiac rhythm management devices are usually microprocessor-based devices whose normal operation can be disrupted by fault events, either arising from a hardware failure or a software problem. The disruption in normal operation, if left unchecked, could cause the device to behave in way which is unsafe for the patient. It is common for CRMD's to incorporate fault detection circuitry which, upon detecting a fault, causes the device to enter a state which is expected to be safe for the patient. For example, a watchdog timer is a hardware timer which runs continuously and is reset periodically by the main control software of the CRMD during normal operation. If a fault disrupts normal operation of the main control software (e.g., a software crash), however, the watchdog timer is allowed to time out and generate a reset signal which re-initializes the system or causes the device to revert to specified operating state. Reset and recovery mechanisms in low-power medical devices historically have been ad hoc designs, attempting to provide limited recovery mechanisms in response to specific fault conditions. These mechanisms can be complex to get to work correctly, and do not effectively respond to unanticipated fault conditions.

In contradistinction to previous systems which employ ad hoc fault recovery mechanisms, the system and method described herein employs a global fault response which enables a CRMD to consistently recover from transient faults while maintaining a history of the reason for the device fault. System resets are generated within the device by either software or hardware as the global fault response. Upon detection of a fault, the primary controller signals the reset controller which then issues a reset command. All sub-systems of the primary device controller are then reset together rather than resetting individual sub-systems independently to ensure deterministic behavior. In an exemplary embodiment, described in greater detail below, a primary device controller providing full-capability diagnostics and therapy in the device is interfaced to a reset controller which manages the reset process. A fail-safe sub-system, referred to below as a safety core, is an optional secondary system that can provide limited therapy as backup while the reset process proceeds. Prior to issuing the reset command, the reset controller causes primary device operation to halt, enables a back-up therapy subsystem, causes the primary controller to log the failure condition prior to initiation of the reset process. However, if the fault interferes with the ability of the device to perform logging, the reset process will occur unconditionally. The activation of the back-up therapy subsystem also occurs unconditionally, independent of the success or failure of the logging process. During the reset process, the primary therapy system executes a complete self-test and re-initialization, to ensure that the primary system is functioning correctly, before returning control to that component. If the self-test fails, the device remains on the back-up therapy subsystem.

1. Exemplary Implantable Device Description

Implantable cardiac rhythm management devices such as pacemakers and cardioverter/defibrillators are battery-powered devices which are usually implanted subcutaneously on the patient's chest and connected to electrodes by leads threaded through the vessels of the upper venous system into the heart. FIG. 1 illustrates an implantable device 105 which may be, for example, a pacemaker capable of delivering bradycardia, resynchronization and/or anti-tachycardia pacing, an implantable cardioverter/defibrillator, or a combination pacemaker/defibrillator. The device is equipped with one or more other leads 110 having electrodes incorporated therein for sensing cardiac electrical activity and/or delivering electrical stimulation to the heart. The leads 110 are adapted to be intra-vascularly disposed in an accessible location of the venous system or within a heart chamber. For example, lead/electrodes may be disposed in the right atrium, right ventricle and in a cardiac vein for sensing cardiac activity and/or delivering pacing pulses to the right atrium, right ventricle, and left ventricle, respectively. The device 105 includes a hermetically sealed housing 130, formed from a conductive metal, such as titanium. Housing 130 (also referred to as a "case" or "can") may be substantially covered over its entire surface by a suitable insulator, such as silicone rubber, except for at a window that forms a third electrode, referred to as a "case" or "can" electrode. A header 140, which may be formed of an insulating material, is mounted on housing 130 for receiving the leads 110. The leads 110 are routed through a sealed feedthrough and connected to electronic circuitry 135 contained within the housing 130 which generates pacing pulses or shock pulses in response to sensed cardiac activity. An electrode can be incorporated into a sensing channel that generates an electrogram signal representing cardiac electrical activity at the electrode site and/or incorporated into a pacing or shocking channel for delivering pacing or shock pulses to the site. A pacing channel is made up of a pulse generator connected to an electrode while a sensing channel is made up of a sense amplifier connected to an electrode. A MOS switch matrix may be used to switch the electrodes from the input of a sense amplifier to the output of a pulse generator as well as allow the sensing and pacing channels to be configured by the controller with different combinations of the available electrodes.

Figure 2:
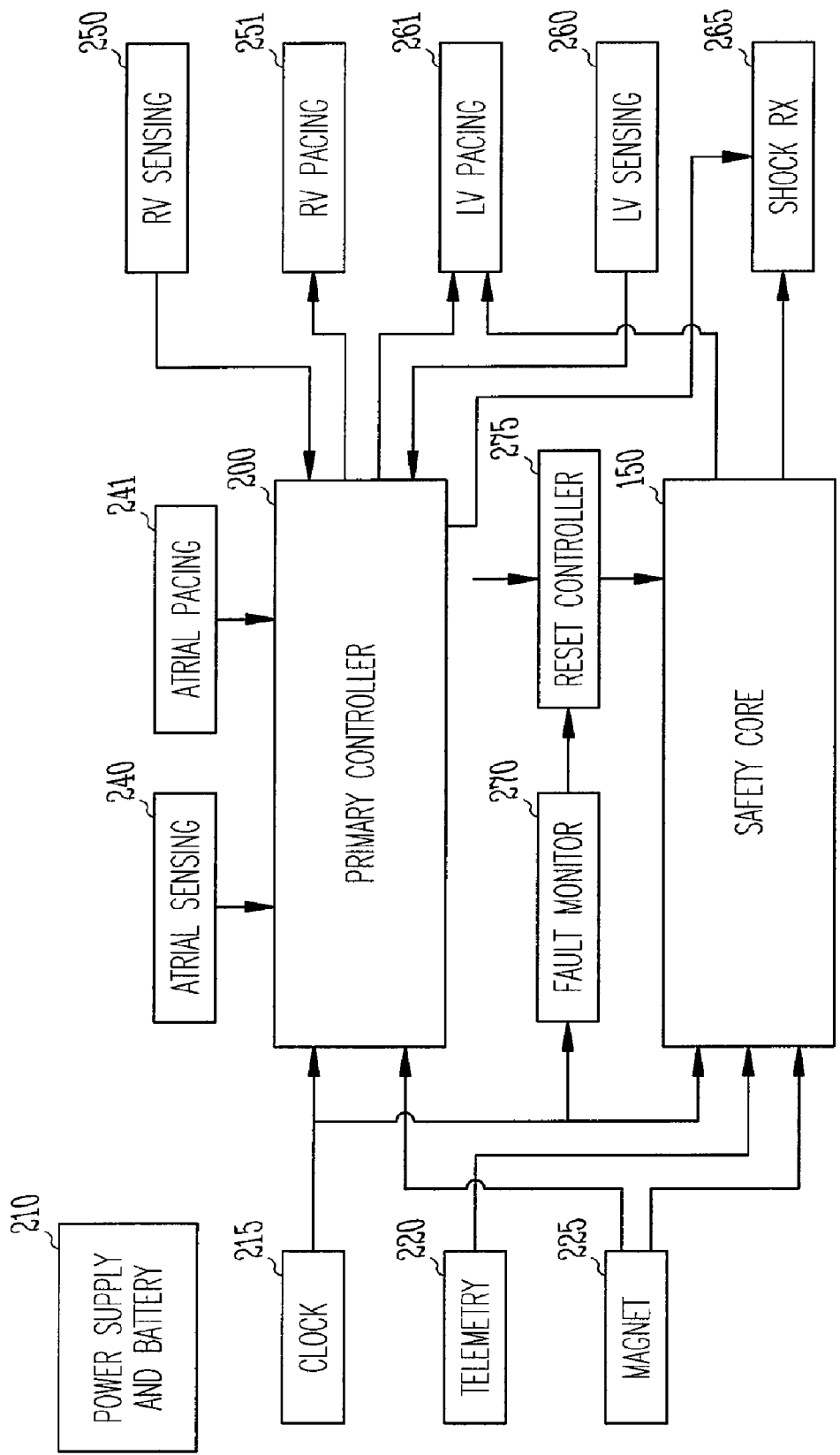
FIG. 2 is a system diagram of exemplary electronic circuitry used to deliver therapy and recover from system faults.

The components of electronic circuitry 135 are illustrated in FIG. 2. A primary controller 200 is made up of a microprocessor and associated memory for program and data storage. The primary controller 200 and other electronic circuitry is powered by a battery and power supply 210. A clock 215 generates timing pulses which drive the controller 200 and other hardware timers of the device. A telemetry system 220 is also provided which enables the controller 200 to communicate with an external device such as an external programmer via a wireless telemetry link. Another means for communication with the device is provided by magnetically actuated switch 225 which is interfaced to the controller 200 and actuated when a magnet is placed in proximity to the device.

The primary controller 200 controls the overall operation of the device in accordance with programmed instructions stored in memory, including controlling the delivery of paces via the pacing channels, interpreting sense signals received from the sensing channels, and implementing timers for defining escape intervals and sensory refractory periods. The pulse generator circuit of each pacing channel is interfaced to the controller 200 so that the output of pacing pulses is under program control. The sensing circuit of each sensing channel is interfaced to the controller and includes a sense amplifier connected to an electrode and a threshold comparator. In FIG. 2, three sensing circuits 250, 240, and 260 are provided for sensing the right ventricle, the right atrium, and the left ventricle, respectively. Three pulse generator circuits 251, 241, and 261 are provided for pacing the right ventricle, the right atrium, and the left ventricle, respectively. A shock pulse generator 265 is also interfaced to the controller to enable delivery of a cardioversion/defibrillation shock. A sensing circuit detects a chamber sense when an electrogram signal (i.e., a voltage sensed by an electrode representing cardiac electrical activity) generated by a particular channel exceeds a specified intrinsic detection threshold. A chamber sense may be either an atrial sense or a ventricular sense depending on whether it occurs in an atrial or a ventricular sensing channel. Pacing algorithms used in particular pacing modes employ such senses to trigger or inhibit pacing. By measuring the intervals between chamber senses, the device is also able to determine an atrial or ventricular rate, and deliver therapy in the form of a cardioversion/defibrillation shock or anti-tachycardia pacing if a tachyarrhythmia is detected.

The primary controller 200 constitutes the primary control system of the device for providing diagnostics and therapy. Also provided as part of the electronic circuitry 135 are components for enabling fault detection and recovery. A fault monitoring circuit 270 detects various kinds of faults and may include, for example, a watchdog timer, a clock deviation monitor, and circuitry for detecting memory errors. The primary controller 200 may also detect faults related to either the hardware or program execution. When a fault is detected by either the primary controller or the fault monitoring circuit, an input signifying the fault event is provided to reset controller 275. The reset controller manages the reset process in response to the fault and enables operation of safety core 150. The safety core 150 is a hardware-based fail-safe sub-system for controlling the operation of the device in delivering certain types of therapies when the primary controller is halted due to a system fault. For example, the safety core 150 may provide basic pacing therapy, tachyarrhythmia detection, and shock delivery using hardware-based logic which operates independently from the primary controller.

2. System Reset Process

Figure 3:
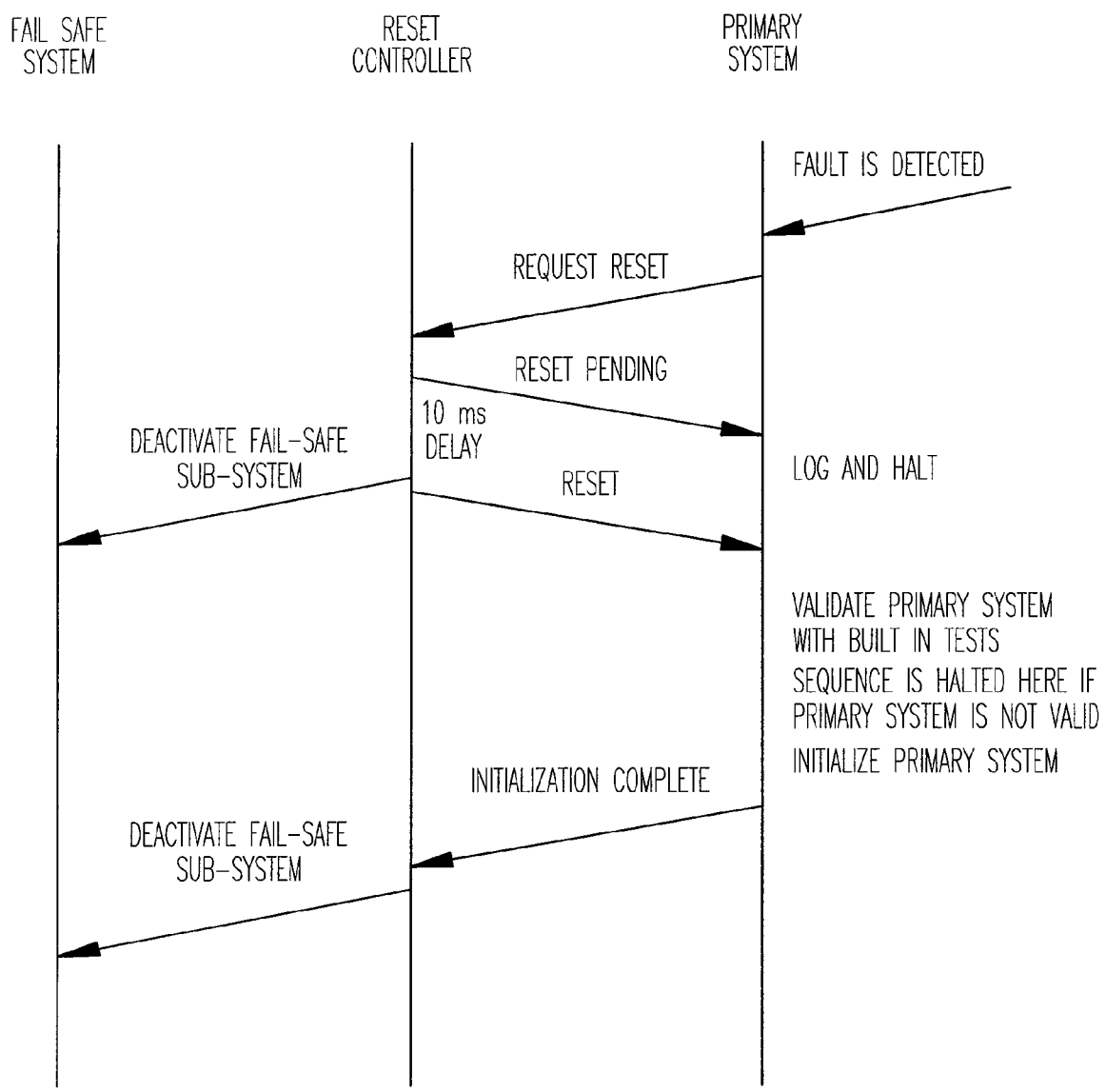
FIG. 3 illustrates an exemplary reset sequence.

The reset sequence, as illustrated by FIG. 3 is initiated when the primary controller 200 or the fault monitoring circuitry 270 detects a fault. A system reset is then requested from the reset controller 275. A pending reset signal is raised by the reset controller to initiate logging of the cause of the pending reset by the primary controller along with context information for later analysis. All therapy functions being performed by the primary controller are halted at this time to prevent further abnormal behavior. A delay (e.g., on the order of 10 milliseconds) ensues to allow the logging operation to complete. This time is arbitrarily chosen and may be adjusted within reason to accommodate the logging requirements. The logging operation is performed by the primary controller if possible, but this is not guaranteed as the fault leading to the system reset may be so severe that no further operation is possible. A reset signal is subsequently raised to the primary system to initiate built-in self-tests used to validate the primary system. The fail-safe sub-system, if one exists, is reset and activated by the reset controller 275 to continue providing service as needed by the device. If the system is validated, the primary system is allowed to re-initialize and resume operation. When the initialization process has successfully completed, the reset controller deactivates the fail-safe sub-system.

The operation of the reset controller may be optionally modified to provide improved tolerance to system faults by incorporating a system-reset monitor which detects system resets caused by non-recoverable and persistent faults. The system-reset monitor provides a mechanism to bound repeated system resets that may occur as a result of faults that are not corrected by system resets and helps to prevent denial of therapy due to non-recoverable and persistent faults. As described above, either software or hardware within the device may generate internal resets which are used to reset the system in an attempt to recover from a transient fault. Telemetry from external equipment may generate resets, referred to as external resets. In this embodiment, a reset count maintained by the system-reset monitor is incremented when an internal reset occurs and is cleared by an external reset. The reset count is decremented by one count every 48 hours (or other specified time period), where the 48 hour time period starts from the first reset and stops when the reset count is zero. Since many system tests are executed daily, this allows faults that occur daily to eventually trip the monitor. The 48 hour time period also provides some margin for delay of daily tests. A non-recoverable or persistent fault is detected when a specified number of (e.g., three) internal resets occur within a 48-hour period. When a non-recoverable or persistent fault is detected, the system-reset monitor inhibits further attempts to restart the primary system and allows the fail-safe backup system to maintain therapy indefinitely without interruption. The system-reset monitor logs the three most recent resets in a FIFO buffer. As the reset count is decremented, the oldest logged event is deleted, and external resets clear the entire buffer. The logged resets may be interrogated with telemetry. The system-reset monitor is disabled once it has tripped to prevent subsequent internal resets from overwriting data and is re-enabled with an external reset.

3. Thread Monitor

In a further enhancement, the fault recovery system includes a thread monitor for monitoring program behavior in the primary controller. Such a thread monitor may be used in any implantable medical device that utilizes computer software employing separate thread execution techniques. The function of this monitor is to detect extended thread execution time and thread sequence anomalies, where a thread is defined as one of several paths of execution inside a single process or context. A thread is generally started in response to an event and terminated when the process needs to wait for another event. Threads may execute in either the background or the foreground and may be interrupted.

Current watchdog timers are general purpose systems that are set to a sufficiently long interval to inhibit false detections for the longest running threads. The proposed system bounds the allowable maximum execution time for every thread. Such bounding reduces the exposure time of the system to errant operation. Errant processor behavior can also manifest itself in violations of program execution by failing to abide by established constraints on thread timing and contiguous thread execution (known as cross-thread execution). Current devices do not provide detection capabilities for cross-thread operation. The thread monitor as described herein will detect cross-thread operation resulting from single-event upsets, process faults, firmware design errors, and other causal events resulting in erroneous program execution.

Figure 4:
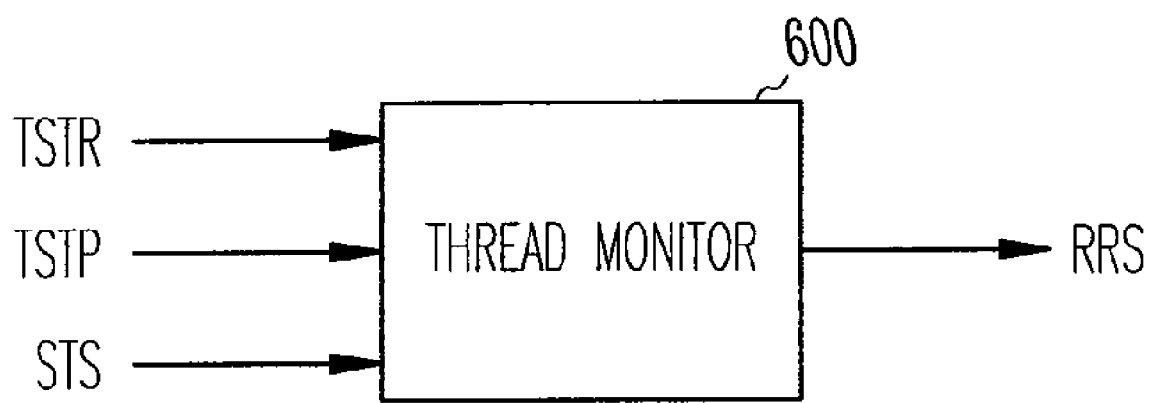
FIG. 4 is a functional block diagram of a thread monitor.

The operation of the thread monitor 600 is illustrated in FIG. 4. Each thread is allocated an identifier ID and a time limit in processor cycles at compile time. This information is used to configure the monitor at the beginning of the thread execution. When the thread is started by the system software, a thread start signal TSTR which includes the thread's ID and time limit is stored in the thread monitor 600. The thread monitor is notified that execution of the thread has completed when it receives a thread stop signal TSTP which also includes the thread's ID. The thread start and stop signals are usually managed by the thread scheduling functions of the system software rather than the thread themselves. A reset request signal RRS is raised if the thread stop signal is not received before the time limit expires or if the start and stop ID's are mismatched. The thread monitor returns the most recent start ID, stop ID, time limit, and remaining time in response to a status STS signal received from the system software in order to provide a context to allow thread interruption. The thread monitor thus provides a way to detect erroneous thread execution in a manner that bounds the thread behavior in terms of time and space. Such fault detection provides a measure of safety not currently available with conventional watchdog timers.

Although the invention has been described in conjunction with the foregoing specific embodiment, many alternatives, variations, and modifications will be apparent to those of ordinary skill in the art. Such alternatives, variations, and modifications are intended to fall within the scope of the following appended claims.

What is claimed is:

1. A method for operating an implantable medical device, comprising:
controlling the operation of the device with a primary controller;
detecting faults with fault monitoring circuitry;
upon detection of a fault by the fault monitoring circuitry, signaling the primary controller to halt operation and to activate a fail-safe subsystem for delivering therapy;
after activation of the fail-safe subsystem, signaling the primary controller to validate its operation with a self-test and to deactivate the fail-safe subsystem if the primary controller is validated; and,
employing a system-reset monitor to detect system resets caused by non-recoverable and persistent faults and to maintain a reset count that is incremented when an internal reset generated by the fault monitoring circuitry occurs, wherein the reset count is intermittently decremented.

2. The method of claim 1 further comprising employing a watchdog timer.

3. The method of claim 1 further comprising monitoring clock deviation.

4. The method of claim 1 wherein the detecting of faults includes detecting memory errors.

5. The method of claim 1 further comprising, upon detection of a fault, signaling the primary controller to initiate logging of possible causes of the fault.

6. The method of claim 5 further comprising providing an input signifying a fault event to a reset controller when a fault is detected by either the primary controller or the fault monitoring circuit.

7. The method of claim 1 further comprising, upon detection of a fault, providing a pending reset signal to initiate logging of the cause of the pending reset by the primary controller.

8. The method of claim 1 wherein the reset count is decremented by one count after expiration of a specified time period until the reset count is zero.

9. The method of claim 1 further comprising detecting a non-recoverable or persistent fault when a specified number of internal resets occur within the specified time period such that a system-reset monitor inhibits further attempts to restart the primary system and allows the fail-safe backup system to maintain therapy indefinitely without interruption.

10. The method of claim 1 further comprising logging recent resets in a FIFO buffer.

11. The method of claim 1 further comprising disabling the system-reset monitor once it has tripped to prevent subsequent internal resets from overwriting data and re-enabling the system-reset monitor with an external reset.

12. A method for operating an implantable medical device, comprising:
   controlling the operation of the device with a primary controller;
   detecting faults with fault monitoring circuitry;
   upon detection of a fault by the fault monitoring circuitry, signaling the primary controller to halt operation and to activate a fail-safe subsystem for delivering therapy;
   after activation of the fail-safe subsystem, signaling the primary controller to validate its operation with a self-test and to deactivate the fail-safe subsystem if the primary controller is validated; and,
   monitoring program behavior in the primary controller by detecting extended thread execution time and thread sequence anomalies, wherein a thread is defined as one of several paths of execution inside a single process or context.

13. The method of claim 12 further comprising allocating to each thread an identifier ID and a time limit in processor cycles at compile time, which information is used to configure the thread monitor at the beginning of the thread execution.

14. The method of claim 12 further comprising providing a thread start signal which includes the thread's ID and time limit that is stored in a thread monitor when a thread is started.

15. The method of claim 14 further comprising providing a thread stop signal which also includes the thread's ID when execution of the thread has completed.

16. The method of claim 15 further comprising a reset request signal that is raised if the thread stop signal is not received before the time limit expires or if the start and stop ID's are mismatched.

17. The method of claim 16 further comprising providing a reset request signal that is raised if the start and stop ID's are mismatched.

18. The method of claim 17 further comprising returning the most recent start ID, stop ID, time limit, and remaining time in response to a status signal received from system software in order to provide a context to allow thread interruption.

* * * * *